(12) United States Patent
Yamakawa et al.

(10) Patent No.: US 6,217,515 B1
(45) Date of Patent: Apr. 17, 2001

(54) IMAGE DISPLAY METHOD AND ULTRASONIC DIAGNOSTIC APPARATUS

(75) Inventors: Tadahiro Yamakawa; Sei Kato, both of Tokyo (JP)

(73) Assignee: Ge Yokogawa Medical Systems, Limited, Tokyo (JP)

( * ) Notice: Subject to any disclaimer, the term of this patent is extended or adjusted under 35 U.S.C. 154(b) by 0 days.

(21) Appl. No.: 09/365,612

(22) Filed: Aug. 2, 1999

(30) Foreign Application Priority Data

Sep. 4, 1998 (JP) .................................................. 10-251555

(51) Int. Cl.$^7$ ....................................................... A61B 8/00
(52) U.S. Cl. ............................................................. 600/437
(58) Field of Search .................................. 600/437, 440, 600/441, 443, 447, 449; 358/335; 73/626, 6; 333/138

(56) References Cited

U.S. PATENT DOCUMENTS 5,477,337 * 12/1995 Sculer .................................... 358/335
5,477,858 * 12/1995 Norris et al. .......................... 600/441

\* cited by examiner

*Primary Examiner*—Francis J. Jaworski
*Assistant Examiner*—Ali M. Imam
(74) *Attorney, Agent, or Firm*—Moonray Kojima

(57) ABSTRACT

In order that an image observed last is ensured to be re-displayed even if an operator inadvertently misses a command to save the image before releasing freeze, an image save processing is activated when the operator commands freeze during cine display, and the latest freeze-displayed image is tagged with a last mark by the image save processing (Step R2). The image tagged with the last mark is automatically saved.

12 Claims, 5 Drawing Sheets

IMAGE DISPLAY METHOD AND ULTRASONIC DIAGNOSTIC APPARATUS

BACKGROUND OF THE INVENTION

The present invention relates to an image display method and ultrasonic diagnostic apparatus, and more particularly to an image display method and ultrasonic diagnostic apparatus which ensures that an image having been displayed at the time of release of freeze can be re-displayed even after the release of the freeze.

A conventional ultrasonic diagnostic apparatus has a normal display mode and a cine display mode.

In the normal display mode, a subject is scanned to obtain successive images which are displayed in real-time. The oldest image stored in a memory is overwritten with the newest image, and data sets for a plurality of the newest images are thus stored in the memory.

In the cine display mode, deletion by the overwriting is stopped, and the plurality of images stored in the memory is sequentially displayed in time order. If a human operator commands freeze during the cine display, the sequential display is suspended, and the image displayed at that time is continuously displayed. If the operator commands rewind during the freeze, the images are traced in inverse time order from the image currently displayed, and when the operator stops the rewind, an image reached at that time is displayed. If the operator commands save of the image, the image displayed at that time is saved. Since that image will not be overwritten or deleted even when the freeze is released to return to the normal display mode, the saved image can be recalled for display any time the operator commands recall.

However, according to the conventional ultrasonic diagnostic apparatus, images other than an image which is specified to be saved are lost from the memory by the overwriting deletion. Thus, such apparatus involves a problem that if the operator inadvertently misses the command to save a necessary image before releasing the freeze, the necessary image is lost and hence re-scanning is required.

SUMMARY OF THE INVENTION

It is an object of the present invention to provide an image display method and ultrasonic diagnostic apparatus which ensures that an image having been displayed at the time of release of freeze can be re-displayed even after the release of the freeze.

In accordance with a first aspect of the invention, there is provided an image display method comprising the steps of: when image display updating is suspended in response to an operator's command during cine display in which a plurality of images stored in a memory are sequentially displayed in time order, automatically saving an image being displayed at that time; and displaying the image in response to an operator's recall command.

According to the image display method of the first aspect, when the operator commands freeze during cine display to suspend the sequential display, an image being displayed at that time is automatically saved. Therefore, even if the operator inadvertently misses a command to save an image before releasing the freeze, the image displayed at the time of the release of the freeze is ensured to be re-displayed.

In accordance with a second aspect of the invention, there is provided the image display method as described regarding the first aspect, comprising the steps of: when a rewind operation is performed for updating the displayed image by tracing images in inverse time order from an image having been displayed during suspending display updating and then the rewind operation is stopped, automatically saving an image being displayed at that time; and displaying the image in response to an operator's recall command.

According to the image display method of the second aspect, when the operator commands freeze during cine display and then rewinds images, the resulting image displayed after the rewind is automatically saved. Therefore, even if the operator inadvertently misses a command to save an image before releasing the freeze, the image displayed at the time of the release of the freeze is ensured to be re-displayed.

In accordance with a third aspect of the invention, there is provided an ultrasonic diagnostic apparatus comprising: an ultrasonic probe; transceiver means for driving the ultrasonic probe to scan a subject with ultrasound and acquire acoustic line data; signal processing means for generating an image data set based on the acoustic line data for one image; storage means for storing a plurality of the newest image data sets; cine display means for sequentially displaying the plurality of stored images in time order; freeze means for suspending image display updating by the cine display means in response to an operator's command; automatic image save means for automatically saving an image being displayed at the time of the suspension; and automatically saved image recall means for displaying the image automatically saved by the automatic image save means in response to an operator's recall command.

The ultrasonic diagnostic apparatus of the third aspect can suitably implement the image display method as described regarding the first aspect, and even if the operator inadvertently misses a command to save an image before releasing the freeze, the image displayed at the time of the release of the freeze is ensured to be re-displayed.

In accordance with a fourth aspect of the invention, there is provided the ultrasonic diagnostic apparatus as described regarding the third aspect, comprising: image save means for saving an image according to an operator's input operation to save an image; and image recall means for displaying the image saved in the image save means according to an operator's input operation to recall an image.

In accordance with a fifth aspect of the invention, there is provided the ultrasonic diagnostic apparatus as described regarding the third or fourth aspect, comprising: rewind means for updating a displayed image by tracing images in inverse time order from an image having been displayed during suspending display updating; automatic image save means for automatically saving an image displayed when the rewind by the rewind means is stopped; and automatically saved image recall means for displaying the image automatically saved by the automatic image save means in response to an operator's recall command.

The ultrasonic diagnostic apparatus of the fifth aspect can suitably implement the image display method as described regarding the second aspect, and even if the operator inadvertently misses a command to save an image before releasing freeze, the image displayed at the time of the release of the freeze is ensured to be re-displayed.

That is, according to the image display method and ultrasonic diagnostic apparatus of the present invention, since at least an image freezed and observed last by the operator is automatically saved, at least the image observed at the time of the release of the freeze is ensured to be re-displayed even if the operator inadvertently misses a command to save an image before releasing the freeze. Thus, a need for re-scanning is eliminated unlike the conventional process, thereby improving diagnostic efficiency.

Further objects and advantages of the present invention will be apparent from the following description of the preferred embodiments of the invention as illustrated in the accompanying drawings.

DETAILED DESCRIPTION OF THE INVENTION

The present invention will now be described in more detail with reference to embodiments thereof shown in the accompanying drawings.

Figure 1:
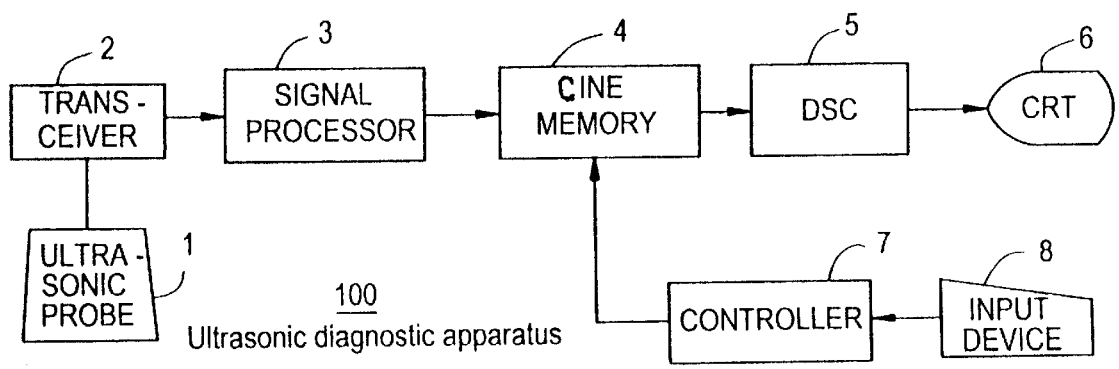
FIG. 1 is a configuration diagram of an ultrasonic diagnostic apparatus in accordance with one embodiment of the present invention.

FIG. 1 is a configuration diagram illustrating an ultrasonic diagnostic apparatus in accordance with one embodiment of the present invention.

The ultrasonic diagnostic apparatus 100 comprises an ultrasonic probe 1, a transceiver section 2 for driving the ultrasonic probe 1 to scan a subject with ultrasound and acquire acoustic line data, a signal processing section 3 for generating an image data set (which may be either in the B-mode, color flow mapping mode or power Doppler imaging mode) based on the acoustic line data for one image, a cine memory 4 for storing a plurality of image data sets, and storing a plurality of the newest image data sets by overwriting the stored oldest image with the newest image, a DSC (digital scan converter) 5 for recalling one of the image data sets from the cine memory 4 to produce a display image, a display unit 6 for displaying the display image, a controller 7 for performing control such as selection of a image data set to be recalled from the cine memory 4 to the DSC 5 (i.e., address control), and an input device 8 for allowing an operator to input several commands such as those to switch between the normal display mode and the cine display mode, and so forth.

Figure 2:
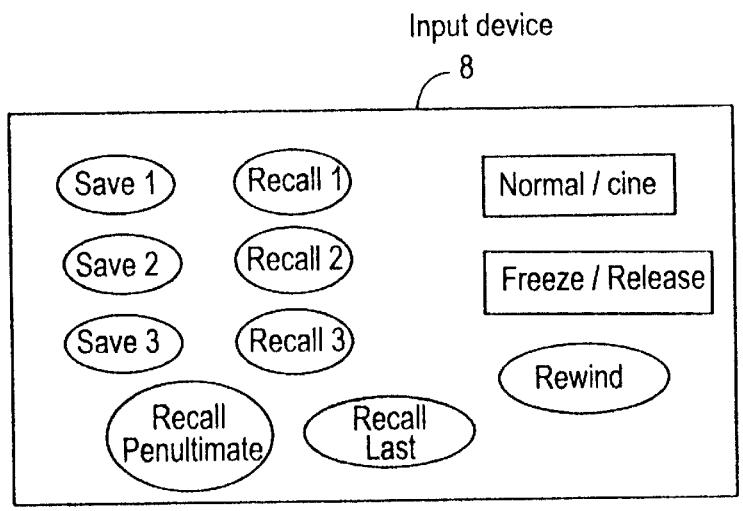
FIG. 2 illustrates a main portion of an input device in the ultrasonic diagnostic apparatus of FIG. 1.

FIG. 2 illustrates a main portion of the input device 8.

The input device 8 includes a 'normal/cine' switch button for performing a switching operation between the normal display mode and the cine display mode, a 'freeze/release' switch button for performing a switching operation between freeze which suspends image display updating during cine display and release of the freeze, a 'rewind' push button for performing an operation to trace images in inverse time order while the button is pressed during the freeze, and to freeze-display an image reached when the button is released, 'save 1', 'save 2' and 'save 3' push buttons for performing an operation to, when one of these buttons is pressed during the freeze, save an image being displayed at that time (i.e., up to three images can be saved), and 'recall 1', 'recall 2' and 'recall 3' push buttons for performing an operation to recall and display the respective images which have been saved using the 'save 1'–'save 3' push buttons.

The input device 8 also includes a 'recall last' push button for performing an operation to recall and display an image having been displayed at the time of release of freeze, and a 'recall penultimate' push button for performing an operation to recall and display an image having been freeze-displayed just before the image displayed at the time of the release of the freeze.

Figure 3:
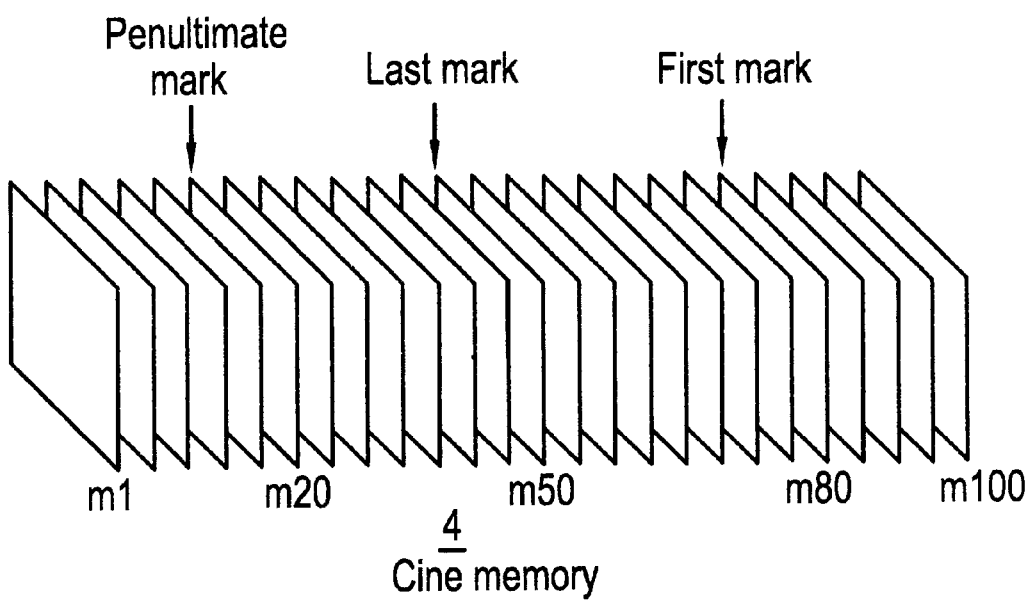
FIG. 3 illustrates a cine memory in the ultrasonic diagnostic apparatus of FIG. 1.

FIG. 3 illustrates a cine memory 4.

Figure 4:
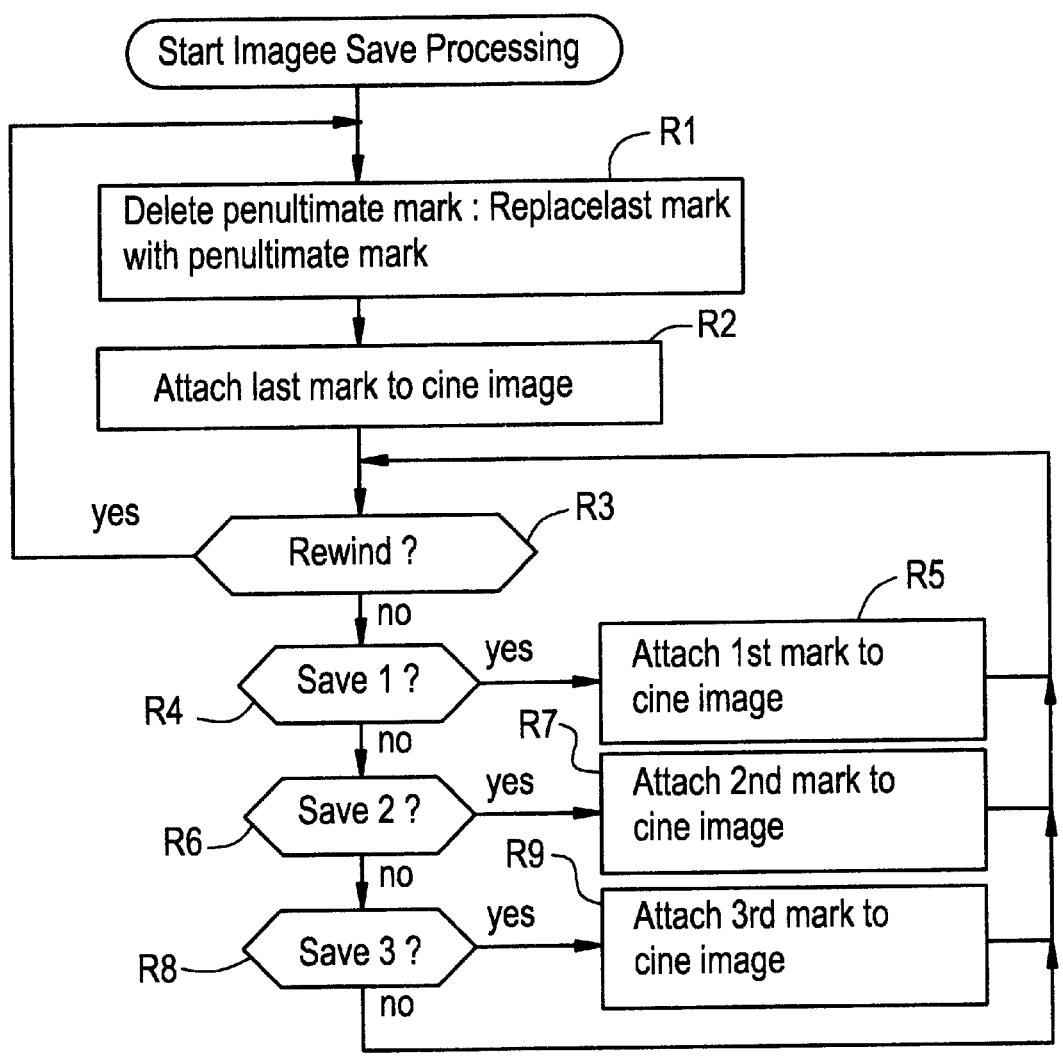
FIG. 4 is a flow chart of an image save processing by the ultrasonic diagnostic apparatus of FIG. 1.

The cine memory 4 consists of, for example, image memories m1–m100 capable of storing a hundred images. The controller 7 sequentially stores images obtained by scanning the subject into the image memories m1–m100 in time order, and when the image memory m100 is reached, the controller 7 sequentially stores images again from the image memory m1 through overwriting. However, the image memories tagged with first–third marks, a last mark or a penultimate mark in an image save processing, which will be described later with reference to FIG. 4, are skipped are not overwritten. In the example shown in FIG. 3, the image memories m80, m50 and m20 are not overwritten. That is, the image data sets in the image memories tagged with the first–third marks, the last mark or the penultimate mark are saved.

When the operator selects the cine display mode, the controller 7 stops storing a new image data set in the cine memory 4, and recalls the images stored in the cine memory 4 in time order for successive display. However, the image data sets in the image memories tagged with the first–third marks, the last mark or the penultimate mark are skipped and are not recalled. An image recall processing for recalling and displaying the image data sets in the image memories tagged with the first–third marks, the last mark or the penultimate mark will be described later with reference to FIG. 5.

FIG. 4 is a flow chart illustrating an image save processing by the ultrasonic diagnostic apparatus 100. The image save processing is activated when the cine display is freezed. For convenience of explanation, the cine memory 4 is assumed to have the image memories m80, m50 and m20 tagged with the first, last and penultimate marks, respectively, immediately before the freeze, as shown in FIG. 3.

In Step R1, the controller 7 deletes the penultimate mark on an image memory and replaces the last mark on another image with the penultimate mark. As exemplarily shown in FIG. 6, the penultimate mark on the image memory m20 is deleted, and the last mark on the image memory m50 is replaced with the penultimate mark.

In Step R2, the controller 7 tags an image memory corresponding to an image being freeze-displayed with the last mark. As exemplarily shown in FIG. 6, if an image in the image memory m60 is displayed during the freeze, the image memory m60 is tagged with the last mark. The first freezed image is thus stored automatically.

In Step R3, if the operator performs rewind, the process goes back to Step R1, otherwise to Step R4.

Figure 6:
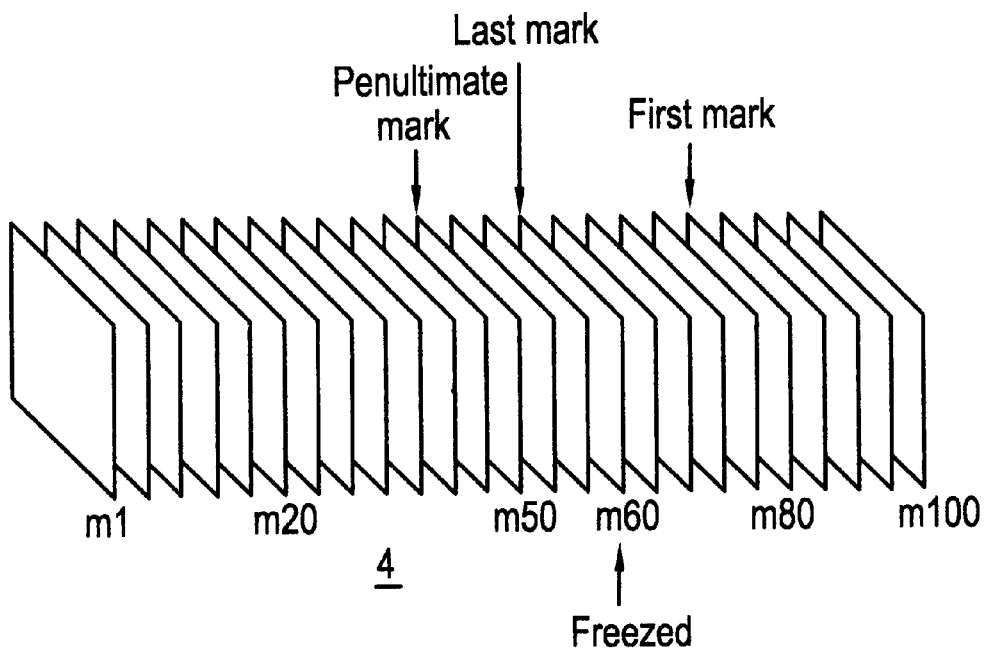
FIG. 6 exemplarily illustrates a marking method when freeze is performed.
Figure 7:
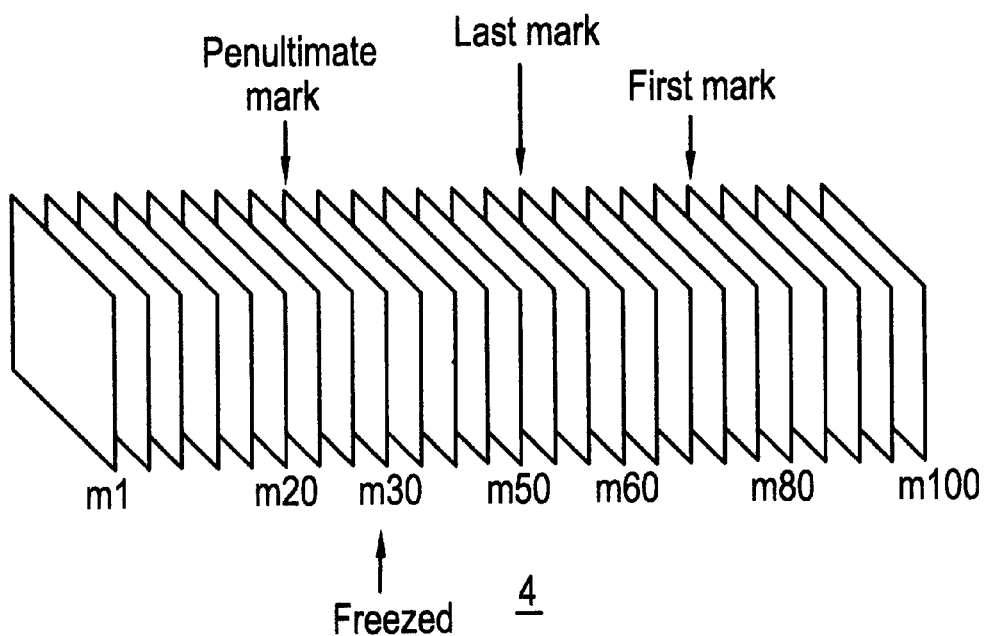
FIG. 7 exemplarily illustrates a marking method when rewind is performed.

For example, if the rewind is performed from the freeze at the image memory m60 shown in FIG. 6 to an image memory m30 shown in FIG. 7, the penultimate mark attached to the image memory m50 is deleted and the last mark attached to the image memory m60 is replaced with the penultimate mark in Step R1, and the last mark is attached to the image memory m30 in Step R2. As a result, the first freezed image and the image after the rewind are stored automatically.

In Step R4, if the operator presses the 'save 1' push button, the process goes to Step R5, otherwise to Step R6.

In Step R5, the controller 7 tags an image memory corresponding to an image being freeze-displayed with the first mark. Then the process goes back to Step R3.

In Step R6, if the operator presses the 'save 2' push button, the process goes to Step R7, otherwise to Step R8.

In Step R7, the controller 7 tags an image memory corresponding to an image being freeze-displayed with the second mark. Then the process goes back to Step R3.

In Step R8, if the operator presses the 'save 3' push button, the process goes to Step R9, otherwise back to Step R3.

Figure 5:
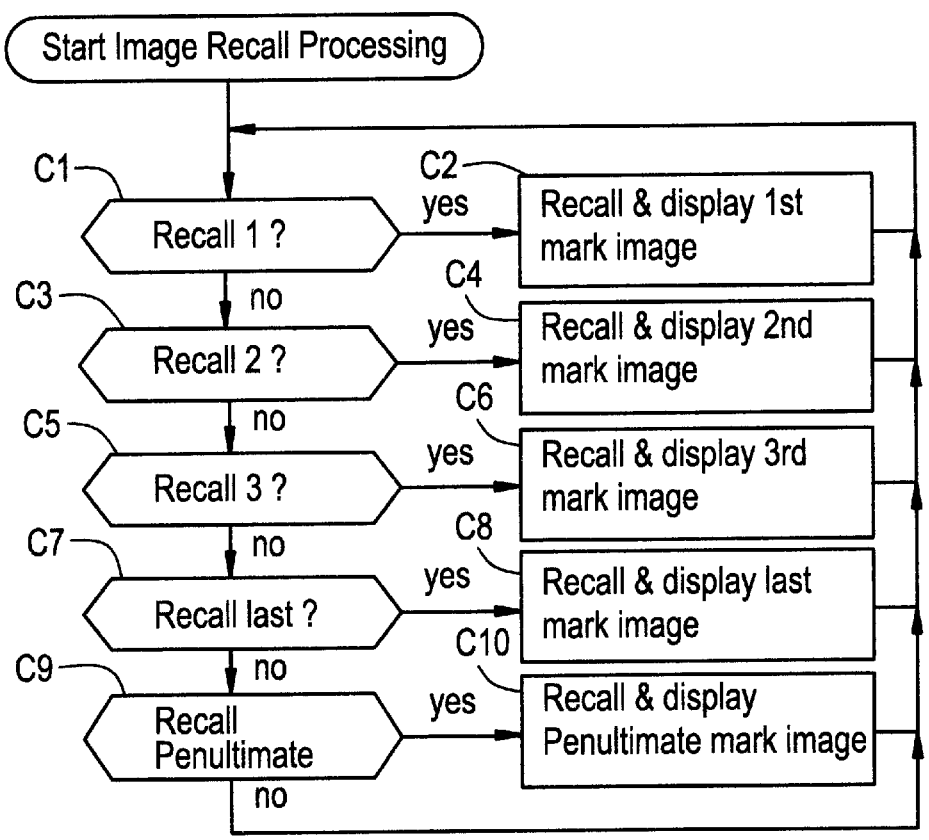
FIG. 5 is a flow chart of an image recall processing by the ultrasonic diagnostic apparatus of FIG. 1.

FIG. 5 is a flow chart illustrating an image recall processing by the ultrasonic diagnostic apparatus 100. The image recall processing is activated when the 'recall 1'–'recall 3' push buttons, the 'recall last' push button or the 'recall penultimate' push button is pressed.

In Step C1, if the operator presses the 'recall 1' push button, the process goes to Step C2, otherwise to Step C3.

In Step C2, the controller recalls an image stored in an image memory tagged with the first mark for display. Then the process goes back to Step C1.

In Step C3, if the operator presses the 'recall 2' push button, the process goes to Step C4, otherwise to Step C5.

In Step C4, the controller 7 recalls an image stored in an image memory tagged with the second mark for display. Then the process goes back to Step C1.

In Step C5, if the operator presses the 'recall 3' push button, the process goes to Step C6, otherwise to Step C7.

In Step C6, the controller 7 recalls an image stored in an image memory tagged with the third mark for display. Then the process goes back to Step C1.

In Step C7, if the operator presses the 'recall last' push button, the process goes to Step C8, otherwise to Step C9.

In Step C8, the controller 7 recalls an image stored in an image memory tagged with the last mark for display. Then the process goes back to Step C1.

In Step C9, if the operator presses the 'recall penultimate' push button, the process goes to Step C10, otherwise back to Step C1.

In Step C10, the controller 7 recalls an image stored in an image memory tagged with the penultimate mark for display. Then the process goes back to Step C1.

According to the ultrasonic diagnostic apparatus 100, since the last image and the image immediately before that image, which were freezed and observed by the operator, are automatically saved, an image observed at the time of release of freeze and an image observed immediately before that image are ensured to be re-displayed even if the operator inadvertently misses a command to save an image before releasing the freeze.

While the preceding description discusses a method of saving image data by tagging an image memory with a mark, a separate save-specific memory may be provided. Moreover, although image data are saved according to the preceding description, display images may alternatively be saved.

Many widely different embodiments of the invention may be configured without departing from the spirit and the scope of the present invention. It should be understood that the present invention is not limited to the specific embodiments described in the specification, except as defined in the appended claims.

What is claimed is:

1. In an image display method comprising the steps of:
   storing a plurality of image data and subsequent storing of image data by overwriting said plurality of stored image data;
   recalling a plurality of image data from storage; and
   displaying in time sequence a display image from said plurality of image data recalled from said storage;
   the improvement comprising the steps of:
   providing at least one mark on at least one selected one of of said plurality of image data in said storage;
   freezing said displaying of said display image of said plurality of image data;
   changing placement of said at least one mark during or at end of said freezing step so that said at least one mark is moved to an image data from said at least one selected one of said plurality of image data in storage so that an image displayed during said freezing step or at end of said freezing step is saved without an operator input at end of said freezing step; and
   subsequently displaying said saved image; whereby
   loss is prevented is an image displayed prior to stopping of freezing without operator input, and repeated scanning is not required to again display an image which would have been otherwise lost.

2. The method of claim 1, further comprising the steps of:
   updating an image being displayed by tracing an image in reverse time sequence for the stored plurality of image data; and
   recalling the image displayed at end of said freezing step from the at least one mark placed on a stored plurality of image data.

3. The method of claim 1, wherein a last mark and a penultimate mark are placed on different ones of said plurality of stored image data; and wherein said penultimate mark is inserted in place of said last mark at end of said freezing step.

4. The method of claim 1, wherein a last mark and a first mark are provided on different ones of said plurality of stored image data; and wherein image data having said first mark is recalled after a rewind operation when images are displayed in reverse time order.

5. The method of claim 1, wherein said freezing step is an updating process wherein a plurality of images from said plurality of store image data are sequentially displayed in time order; and an image being displayed is saved by placement of said at least one mark on said at least one selected image data.

6. The method of claim 1, further comprising a rewinding step wherein said one mark is moved to an image data of said plurality of stored image data at end of said rewinding step, thereby to save an image appearing at end of said rewind step.

7. An ultrasonic diagnostic apparatus comprising:
   an ultrasonic probe;
   transceiver means for driving said ultrasonic probe to scan a subject with ultrasound and acquire line data;
   signal processing means for generating an image data based on said line data for one image;
   storage means for storing in a time sequence a plurality of image data and storing a next plurality of image data by overwriting said plurality of image data priorly stored therein;
   display means for sequentially updating and displaying in time sequence a plurality of images from said plurality of image data stored in said storage means; and controller means for controlling said signal processing means and storage means to cause said display means to display said image, said controller means comprising:

means for providing at least one mark on a selected one of said plurality of stored image data;

means for freezing image display updated by said display means responsive to an operator command;

means for saving a desired image being displayed at time of or at end of a freezing by said means for freezing by moving said at least one mark to an image data of an image being displayed during freezing operation or at end thereof; and means for subsequently recalling said image data being saved;

whereby loss is prevented of an image displayed prior to stopping of freezing and repeated scanning is not required to again display the image which would have otherwise been lost.

8. The apparatus of claim 7, wherein said means for saving operates to automatically save said image being displayed at end of said freezing operating by inserting a penultimate mark in place of a last mark in said plurality of image data stored in said storage means.

9. The apparatus of claim 7, wherein said controller means further comprises means for rewinding to update said display of images in a reverse time sequence; and means for saving an image being displayed during said rewind operating by inserting another mark in image data of an image being displayed during rewind in said plurality of image data stored in said storage means.

10. The apparatus of claim 7, wherein said controller means further comprises: means for updating display of images from said plurality of stored image data; and means for saving an image data being displayed during updating of display by inserting another mark on an image data of said plurality of store image data.

11. The apparatus of claim 7, wherein said means for providing comprises means for providing a last mark and a first mark on different ones of said plurality of stored image data; and wherein said means for saving retains the position of said first mark so that image data having said first mark is recalled after a rewind operation when images are displayed in reverse time order.

12. The apparatus of claim 7, wherein said controller means further comprises an updating means for updating an image being displayed by tracing an image in reverse time sequence for said plurality of stored image data; and wherein said means for subsequently recalling comprises means for recalling an image displayed at end of said freezing operation of said at least one mark placed on a selected one of said plurality of stored image data.

* * * * *